United States Patent [19]

Gottlieb

[11] Patent Number: 5,109,875
[45] Date of Patent: May 5, 1992

[54] RING TISSUE EXPANDERS AND THEIR METHOD OF USE

[75] Inventor: Marc E. Gottlieb, West Covina, Calif.

[73] Assignee: City of Hope, Duarte, Calif.

[21] Appl. No.: 517,841

[22] Filed: May 2, 1990

Related U.S. Application Data

[63] Continuation of Ser. No. 262,063, Oct. 24, 1988, abandoned, which is a continuation of Ser. No. 920,616, Oct. 20, 1986, abandoned.

[51] Int. Cl.⁵ .............................................. A61B 19/00
[52] U.S. Cl. ................................... 128/899; 128/898; 623/8
[58] Field of Search ............................... 128/897–899; 623/8

[56] References Cited

U.S. PATENT DOCUMENTS

| | | | |
|---|---|---|---|
| 2,769,442 | 11/1956 | Stubbs | 128/129 |
| 4,217,889 | 8/1980 | Radovan et al. | 128/899 |
| 4,574,780 | 3/1986 | Manders | 128/899 |
| 4,666,447 | 5/1987 | Smith et al. | 128/1 R X |
| 4,685,447 | 8/1987 | Iversen et al. | 128/1 R |

Primary Examiner—C. Fred Rosenbaum
Assistant Examiner—Corrine Maglione
Attorney, Agent, or Firm—Edward S. Irons; Thomas S. Hahn

[57] ABSTRACT

An apparatus and method for treating skin lesions using an expansion chamber surgically implanted under the skin and progressively filled with fluid for growing new skin along the entire circumference surrounding the skin lesion so that upon removal of the expansion chamber the new skin radially contracts over the lesion.

2 Claims, 1 Drawing Sheet

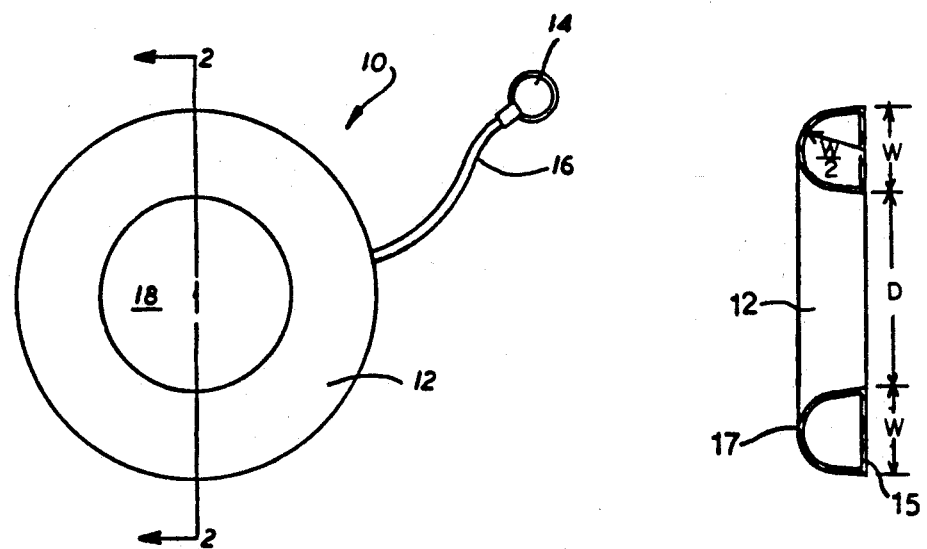
FIG. 1
FIG. 2
FIG. 3
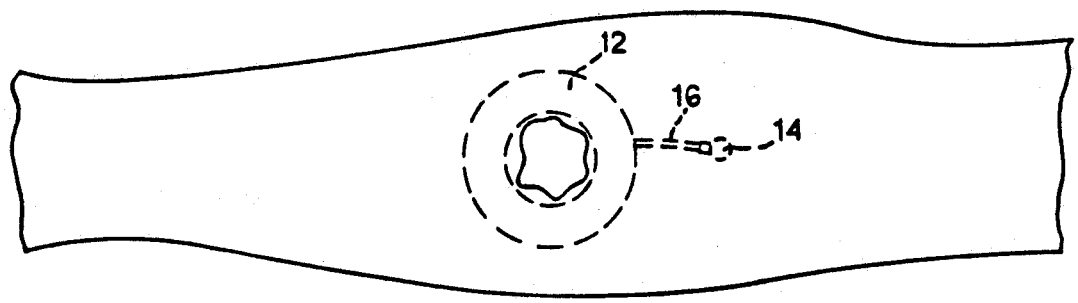
FIG. 4
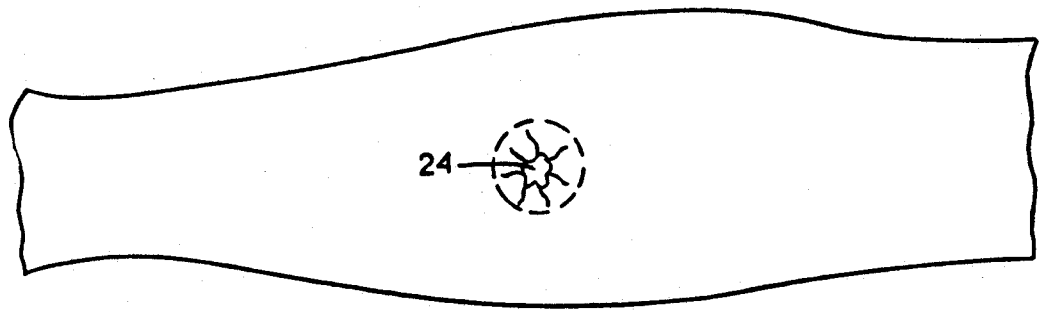
FIG. 5
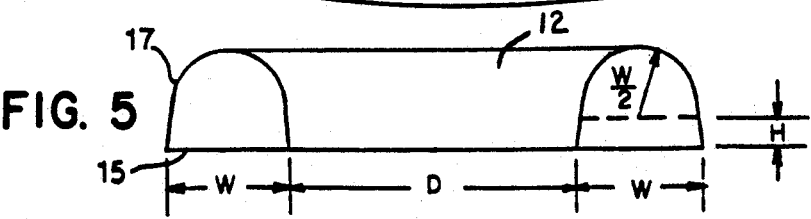

RING TISSUE EXPANDERS AND THEIR METHOD OF USE

This application is a continuation of Ser. No. 262,063, filed Oct. 24, 1988 now abandoned, which is a continuation of Ser. No. 920,616, filed Oct. 20, 1986, now abandoned.

BACKGROUND OF THE INVENTION

A. Field of the Invention

This invention relates to apparatus and methods for use with tissue expanders in the surgical treatment of skin lesions. In particular, this invention relates to use of ring-shaped tissue expanders which induce growth of skin in an annular geometry about a lesion so that on removal of the ring-shaped tissue expanders, the new skin contracts in radial directions to the center of the annulus to close the lesion.

B. Description of the Prior Art

It is a well known fact that skin and subcutaneous tissue expands. In medical practice, this physiological phenomenon is observed daily. Examples include skin progressively expanding over an underlying hematoma or a slowly growing tumor.

Providing extra skin tissue for reconstructive surgery by implanting an inflatable envelope connected to an external tube for injecting fluid into the envelope has been reported as early as 1957 (See, Neumann, C. G., The Expansion of an Area of Skin by Progressive Distention of the Subcutaneous Balloon, *Plast.Reconstr..Surg.*, 19:124, 1957.) Substantial use of inflatable envelopes did not follow the work of Neumann.

In the mid-1970's, however, Dr. Chedomir Radovan disclosed an implantable, inflatable envelope for inducing growth of new skin with a semi-rigid backplate attached to the expandable envelope and a connected self-sealing remote injection port (See, e.g., U.S. Pat. No. 4,217,889, entitled Flap Development Device and Method of Progressively Increasing Skin Area, issued Aug. 19, 1980 to Chedomir Radovan, and Rudolf R. Schulti; and Radovan, C. Reconstruction of the Breast after Radical Mastectomy Using Temporary Expander, *Plast.Surg.Forum*, 1:41, 1978). Subsequent to Radovan's work, Eric Austad developed self-inflating soft tissue expanders having permeable envelopes enclosing a high solute load. By osmosis the solute is diluted by body fluids which causes a slow expansion without the need for periodic injections (See, U.S. Pat. No. 4,157,085 entitled Surgically Implantable Tissue Expanding Device and the Method of its Use, issued Jun. 5, 1979 to Eric Austad).

The use of inflatable envelopes to induce growth of new skin and subcutaneous tissue has been found useful in surgical breast reconstruction, and for providing adjacent skin flaps for use in plastic surgery and in the surgical removal of tattoos, benign processes such as lymphangiomes and large scars. Having new skin and subcutaneous tissue grown for use adjacent to the area of growth has the advantages of providing essentially identical skin which matches both the skin color and texture of the skin in the area to be healed. This degree of skin matching is not always achieved in skin grafting where skin is taken from a different part of a patient and transplanted to a second location.

SUMMARY OF THE INVENTION

Prior treatment of skin lesions by surgeons using inflatable envelopes to induce growth of new skin and subcutaneous tissue is practiced by having the new skin used as a flap. A flap is an area of skin with its underlying subcutaneous tissue disconnected from the underlying and surrounding tissue except at one edge. The flap is stretched and applied to an adjacent recipient area while it remains connected to adjacent tissue at the original edge. Use of such flaps unavoidably results in large deforming linear scars.

The invention disclosed and claimed here eliminates the deforming linear scars which result from use of skin flaps. Unlike the previous use of inflatable envelopes as tissue expanders which cause new skin and subcutaneous tissue to grow adjacent only one side of the area where the skin is to be used, the present invention provides new skin and subcutaneous tissue radially about the entire circumference around a lesion. To so provide new skin and subcutaneous tissue, a ring-shaped expander is implanted beneath the subcutaneous layer with the lesion to be treated centered in the ring expander. After the new skin and subcutaneous tissue has grown and the ring expander has been removed, the new skin and subcutaneous tissue will contract toward the center and cover the area previously exposed by the lesion. Depending on the size of the lesion, and the amount of new skin grown additional implantation of ring expanders can be used to effect complete treatment for large lesions.

BRIEF DESCRIPTION OF THE DRAWINGS

The novel features of the invention will be more readily appreciated from the following description when read in conjunction with the appended drawings, in which corresponding components are designated by the same reference numerals throughout the various figures.

FIG. 1 is a top plan view of a ring tissue expander according to the present invention;

FIG. 2 is a cross-sectional side view of the ring tissue expander shown in FIG. 1 as taken along line 2—2 showing the inside of the expansion chamber;

FIG. 3 is a schematic view of a patient's arm with a ring tissue expander of the present invention implanted around a lesion to be treated;

FIG. 4 is a schematic view of the patient's arm from FIG. 3 after the ring tissue expander has been removed and the new skin and subcutaneous tissue has contracted toward the center of the lesion; and FIG. 5 is a cross-sectional side view of an alternative ring expander of the present invention having an increased expansion chamber volume.

DETAILED DESCRIPTION OF THE INVENTION

A ring tissue expander according to the present invention is shown in FIG. 1 where it is generally designated by reference numeral 10. The ring tissue expander 10 is so constructed as to include fluid expansion chamber 12 and a fluid injection port 14 with connecting tube 16 for providing fluid to fill the expansion chamber 12. The expansion chamber 12 is formed from a semi-rigid bottom plate 15 and a flexible upper wall 17 (see FIG. 2).

According to the present invention, the expansion chamber 12 is constructed so as to be a closed ring with a central area 18 surrounded by the expansion chamber 12.

To treat skin lesions by the present invention, which for example can be associated with a burn scar, tatoo removal, or hairy nevus removal, an incision is made adjacent a skin lesion 20 and a ring expander 10 is positioned beneath the subcutaneous layer with the skin lesion 20 surrounded by the expansion chamber 12 of the ring expander 10 (see FIG. 3). After installation of the ring expander 10 about the skin lesion 20, fluid is progressively injected into the expansion chamber 12. The expansion chamber 12 as it is filled with fluid induces growth of new skin and subcutaneous tissue about the entire circumference of the skin lesion 20. When the growth of new skin and subcutaneous tissue has conformed to a fully inflated expansion chamber 12, the ring expander 10 is removed and the new skin and subcutaneous tissue contracts toward the center of the lesion 20 in response to normal compressive radial forces resulting from the void provided by the lesion 20. Initially there will be a puckering of the new skin contracted over the lesion 20, but over time the contracted skin will conform to the patient's body contour in the region of the lesion 20.

Contemporaneous with the abating of skin puckering, there will be a scar 24 formed in the central region of the lesion 20 where the contracted skin has not migrated (see FIG. 4). This scar 24 will have a surface area smaller than that of the lesion 20. However, depending on the original surface area of lesion 20 and the amount of new skin and subcutaneous tissue grown by the ring expander 10 the scar 24 at the center of the original lesion 20 could still be unacceptably large. The scar 24 can be reduced in size by a second use of a smaller ring expander 10 in the same manner as the first use. Specifically, a ring expander 10 is inserted under the patient's skin with the expansion chamber 12 encircling the scar 24. After new skin and subcutaneous tissue has grown over the expansion chamber 12, the ring expander 10 is removed and the new skin and subcutaneous tissue contracts toward the center where a smaller scar will form.

The procedure of progressively using smaller ring expanders 10 to decrease the area of scar tissue can be repeated until the scar is either essentially not visible or is of such size as to be acceptable.

The relationship of the diameter, D, of the central area 18 of a ring expander 10 to the width, W, of the expansion chamber 12 determines the amount of new skin which contracts over a lesion 20 (see FIG. 2). If the cross sectional area of expansion chamber 12 is half a circle then the amount of new skin and subcutaneous tissue grown above the expansion chamber 12 which will be available for covering the lesion 20 will be essentially equal to the surface area of the half circular toriod shaped expansion chamber 12 minus the undistended surface area of the skin where the ring expander 10 was positioned before inflation of the expansion chamber 12. Written in terms of the diameter, D, of the central area 18 of the ring expander 10 and the width, W, of the expansion chamber 12 this surface area is:

$$\frac{\pi W}{4}\left[\frac{D}{2}(\pi - 2) + W(\pi - 1)\right]$$

Since the surface area of a lesion 20 in the central-area 18 of a ring expander 10 is essentially equal to $$\pi \frac{D^2}{4},$$

the relationship of the diameter, D, of a ring expander 10 to the width, W, of the expansion chamber 12 can be selected to have the area of new skin and subcutaneous tissue equal the surface area of the lesion 20. However, the annular geometry of the new skin precludes having the new skin contract over an equal circular area of lesion 20.

As the size of lesion 20 increases the amount of puckering of contracting skin also increases. Therefore, the size of the ring expander 10 is traded off against the amount of puckering and the size of the resulting scar tissue.

To aid in assuring the optimum growth of new skin and subcutaneous tissue the cross-sectional area of an alternate preferred embodiment for expansion chamber 12 includes an additional height, H, in the upper wall 17 to compensate for the expansion chamber 12 being downwardly displaced against patient's body when new skin is grown. Thus an optimum cross-sectional area for expansion chamber 12 is provided to assure optimum growth of new skin.

Though the expansion chamber 12 has been described as having a circular shaped bottom plate 15, of diameter D, this bottom plate 15 can also be oval shaped. The oval shape must be continuous and closed to assure growth of new skin which will radially contract over a lesion. The oval shape facilitates use of a ring expander 10 for treatment of lesions which are not strictly circular in area but are oblong. The use of ring expanders 10 with oval shaped bottom plates 15 will result in essentially oval shaped scars. After these oval shaped scars have been reduced in size a circular shaped ring expander 10 can be used to further reduce the size of the scars until a cosmetically acceptable scar is obtained.

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A procedure for reducing the size of a first epidermal scar which comprises:
   (i) surrounding said first scar with the expansion chamber of a surgically implanted device to induce the growth of new skin overlaying the surface of said expansion chamber and extending around the perimeter of said scar;
   (ii) removing the implanted device and permitting the new skin to contract inwardly, thus producing a smaller, second epidermal scar; and
   (iii) reducing said smaller scar by at least one repetition of steps (i) and (ii) with a smaller surgically implanted device having an expansion chamber.

2. The procedure defined by claim 1 in which each surgically implanted device is generally ring shaped, is implanted below the surface of the skin adjacent the perimeter of the scar to be reduced and comprises:
   a flat base member having an open central region to accommodate a scar to be reduced,
   said base member having attached thereto a flexible upper member surrounding said central region and defining an expansion chamber of arch-like cross-section when expanded, and
   means for progressively expanding said chamber by the introduction of fluid in controlled volume.

* * * * *